United States Patent
Frojdh et al.

(10) Patent No.: US 10,551,303 B2
(45) Date of Patent: *Feb. 4, 2020

(54) FLOW CELL OPTICAL DETECTION SYSTEM

(71) Applicant: GE HEALTHCARE BIO-SCIENCES AB, Uppsala (SE)

(72) Inventors: Hakan Frojdh, Uppsala (SE); Mikael Hornqvist, Uppsala (SE); Stig Tormod, Uppsala (SE); Patrik Akerstrom, Uppsala (SE)

(73) Assignee: GE HEALTHCARE BIO-SCIENCES AB, Uppsala (SE)

(*) Notice: Subject to any disclaimer, the term of this patent is extended or adjusted under 35 U.S.C. 154(b) by 20 days.

This patent is subject to a terminal disclaimer.

(21) Appl. No.: 15/633,678

(22) Filed: Jun. 26, 2017

(65) Prior Publication Data

US 2017/0292909 A1    Oct. 12, 2017

Related U.S. Application Data

(63) Continuation of application No. 13/130,166, filed as application No. PCT/SE2009/051321 on Nov. 23, 2009, now Pat. No. 9,719,917.

(Continued)

(51) Int. Cl.
*G01N 21/33* (2006.01)
*G01J 3/02* (2006.01)
(Continued)

(52) U.S. Cl.
CPC ............ *G01N 21/33* (2013.01); *G01J 3/0218* (2013.01); *G01J 3/42* (2013.01); *G01N 21/05* (2013.01);
(Continued)

(58) Field of Classification Search
CPC ........... G01N 21/33; G01N 2021/3133; G01N 21/314; G01N 21/51; G01J 3/0291; G01J 3/0202
See application file for complete search history.

(56) References Cited

U.S. PATENT DOCUMENTS 3,503,683 A    3/1970  Isreeli et al.
3,917,404 A    11/1975 Heiss
(Continued)

FOREIGN PATENT DOCUMENTS

DE    4112528 A1    10/1992
JP    06-094946     4/1994
(Continued)

OTHER PUBLICATIONS

Office Action Received for Japanese Patent Application No. 2011537398, dated Jan. 8, 2014, 6 pages (3 pages of official copy + 3 pages of English translation).
(Continued)

*Primary Examiner* — Rebecca C Bryant
(74) *Attorney, Agent, or Firm* — Wood IP LLC (57) ABSTRACT

The present invention discloses a flow cell optical detection system comprising a light source, a flow cell and a light detector, wherein the light detector is arranged in a separate detector unit that is arranged to be releasably attached to a detector interface, the detector interface being in optical communication with the light source and comprises optical connectors for optically connecting the flow cell and the detector unit in the light path from the light source, and wherein the flow cell is an interchangeable unit arranged to be held in position by the detector unit when attached to the detector interface.

20 Claims, 10 Drawing Sheets

Related U.S. Application Data (60) Provisional application No. 61/117,261, filed on Nov. 24, 2008.

(51) Int. Cl.
*G01N 21/05* (2006.01)
*G01J 3/42* (2006.01)
*G01N 21/51* (2006.01)
*G01J 3/433* (2006.01)
*G01N 21/03* (2006.01)

(52) U.S. Cl.
CPC ............ *G01J 3/0291* (2013.01); *G01J 3/433* (2013.01); *G01N 21/51* (2013.01); *G01N 2021/0346* (2013.01); *G01N 2201/061* (2013.01); *G01N 2201/086* (2013.01); *G01N 2201/0853* (2013.01)

(56) References Cited

U.S. PATENT DOCUMENTS

| | | | |
|---|---|---|---|
| 5,492,673 A * | 2/1996 | Curtis | B01L 3/021 422/922 |
| 5,572,031 A | 11/1996 | Cooper et al. | |
| 6,526,188 B2 | 2/2003 | Dourdeville et al. | |
| 7,667,837 B2 | 2/2010 | Iwano et al. | |
| 8,125,626 B2 | 2/2012 | Furtaw | |
| 9,404,849 B2 * | 8/2016 | Wynn | G01N 21/05 |
| 2003/0156292 A1 | 8/2003 | Naya | |
| 2003/0191405 A1 | 10/2003 | Rich et al. | |
| 2005/0191014 A1 * | 9/2005 | Renfro, Jr. | G02B 6/2551 385/99 |
| 2005/0286054 A1 | 12/2005 | Chen et al. | |
| 2012/0127456 A1 | 5/2012 | Frojdh et al. | |

FOREIGN PATENT DOCUMENTS

| | | |
|---|---|---|
| JP | 09-101260 A | 4/1997 |
| JP | 2004-340636 A | 12/2004 |
| WO | 2007/062800 A1 | 6/2007 |
| WO | 2010/059121 A1 | 5/2010 |

OTHER PUBLICATIONS

Supplementary European Search Report for EP Application No. EP09827833.6-1554, dated Dec. 12, 2017, 4 pages.

\* cited by examiner

FLOW CELL OPTICAL DETECTION SYSTEM

FIELD OF THE INVENTION

The present disclosure relates to a flow cell optical detection system of modular design.

BACKGROUND OF THE INVENTION

Flow cell optical detection system, typically comprises a light source for providing light of one or more wavelengths to a fluid sample in a fluid cell and an optical detection system for detecting any interaction between the light and the sample. One example of a flow cell optical detection system is a flow cell UV absorption monitor system that is utilized to measure different absorbance of light at various wavelengths in chromatography systems when separated molecules are eluted from the columns.

Monitor systems of this type usually include a light source, a flow cell and a light detector. Ideally, the flow cell is designed to ensure a signal-to-noise ratio with minimal drift and refractive index sensitivity. However, in some systems the flow cell is externally connected to the light source with optical fibers, whereby it becomes sensitive to external light, temperature difference and movements (e.g. vibrations). The optical fibers are also very fragile and can be cracked if bended. This vibration and temperature fluctuation may lead to problems with the operation of the monitor. Also, the monitors are typically built as one unit where both light source and detector are combined in the same housing. This limits the flexibility of the system and might also give electromagnetic compatibility problems since the light source and sensitive detector electronics are placed in the same housing.

SUMMARY OF THE INVENTION

The object of the invention is to provide a new flow cell UV absorption monitor system, which overcomes one or more drawbacks of the prior art. This is achieved by the flow cell UV absorption monitor system as defined in the independent claim.

One advantage with such a flow cell UV absorption monitor system is that it is easy to switch the interchangeable flow cell preserving reproducible measurement results at the same time as it is simple to replace the detector unit if needed.

Another advantage is that the detector unit may be located at a remote location with respect to the light source.

Further scope of applicability of the present invention will become apparent from the detailed description given hereinafter. However, it should be understood that the detailed description and specific examples while indicating preferred embodiments of the invention are given by way of illustration only. Various changes and modifications within the spirit and scope of the invention will become apparent to those skilled in the art from the detailed description below.

BRIEF DESCRIPTION OF DRAWINGS

These and other advantages of the present invention will become more apparent as the following description is read in conjunction with the accompanying drawings, wherein.

DETAILED DESCRIPTION OF THE PREFERRED EMBODIMENTS

The presently preferred embodiments of the invention are described with reference to the drawings, where like components are identified with the same numerals. The descriptions of the preferred embodiments are exemplary and are not intended to limit the scope of the invention.

Figure 1:
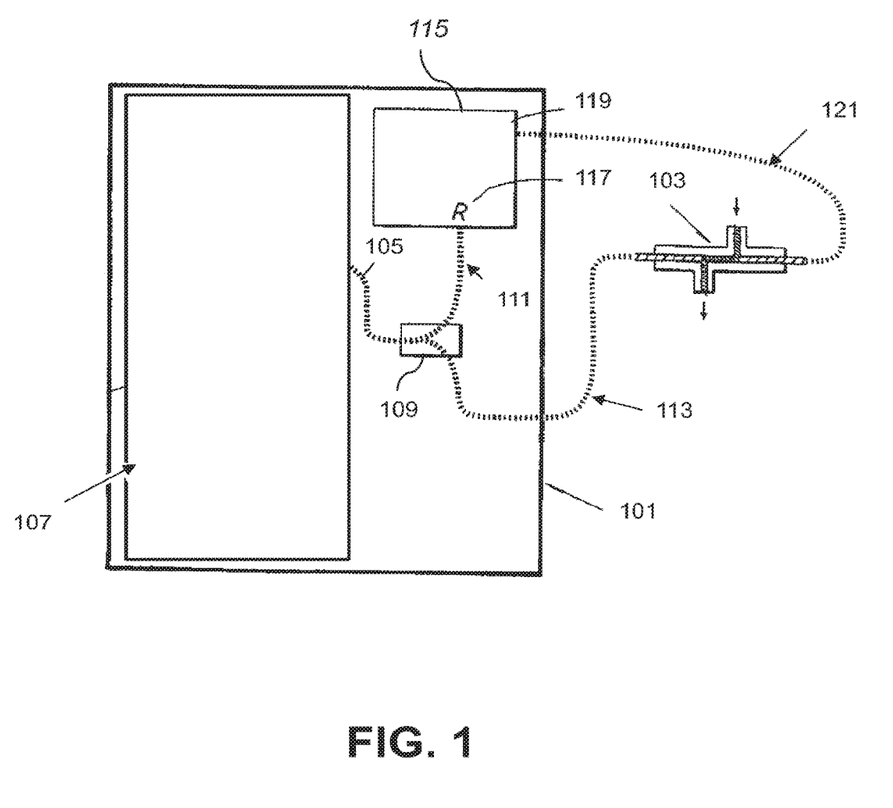
FIG. 1 illustrates a schematic of a typical multi-wavelength monitor.

FIG. 1 illustrates a typical multi-wavelength Ultra-violet (UV)-Visible monitor. This monitor 101 includes an interchangeable flow cell 103 and optical fibers 105. Monitor 101 may e.g. be a Monitor UV-900 manufactured by GE Healthcare, Life Sciences located in Uppsala, Sweden. This monitor utilizes advanced fiber optic technology to monitor light with high sensitivity at up to three wavelengths simultaneously in a range of 190-700 nm. The use of fiber optics together with the unique flow cell design ensures a signal-to-noise ratio with minimal drift and refractive index sensitivity. Typically, the monitor 101 includes a monochromator 107 with a light source (not shown), such as a xenon flash lamp (not shown) that provides a high intensity, continuous spectrum of light, and a tuneable monochromator arrangement (not shown) for selecting the wavelength of light output to the fiber 105. The lamp is activated only during the chromatographic run, ensuring that its long lifetime of approximately 4000 hours of effective operation is used efficiently. In the disclosed monitor 101, the optical fiber 105 optics leads the light from the monochromator 107 to an optical splitter unit 109 splitting the light to a reference fiber 111 and a flow cell fiber 113 leading directly to the flow cell 103 and focus its full intensity on the liquid flow path, thus maximizing the sensitivity of the monitoring. Flow cell 103 may have any path length, such as a path length of 2 mm and cell volume of 2 μl or path length of 10 mm and a cell volume of 8 μl. The transmitted light through the flow cell 103 is guided to a light detection unit 115 detector (not shown) via an optical fiber 121. The light detection unit 115 has a flow cell input 119 connected to fiber 121 and a reference input 117 connected to the reference fiber 111. The detection unit 115 further may comprise suitable processing means for comparing the flow cell input with the reference to detect changes in light absorption in the flow cell.

According to one embodiment shown in FIG. 2, there is provided a flow cell optical detection system 100 comprising a light source 107, a flow cell 201 and a light detector 205, wherein the light detector is arranged in a separate detector unit 201 that is arranged to be releasably attached to a detector interface 215a. The detector interface 215a being in optical communication with the light source 107 and comprises optical connectors 221, 219 for optically connecting the flow cell 211 and the detector unit 201 in the light path from the light source 107. The flow cell 211 is an interchangeable unit arranged to be held in position by the detector unit 201 when attached to the detector interface 215a.

As mentioned above the optical detection system 100 may be an UV-Visible spectrometer monitor. In such embodiments, the light source may be a tuneable monochromatic light source as disclosed schematically above, and referred to as a monochromator 107. In alternative embodiments, the light source 107 may be a non tuneable monochromatic light source, such as a laser diode of suitable wavelength or the like. In other embodiments the light source may be a polychromatic light source.

Figure 2A:
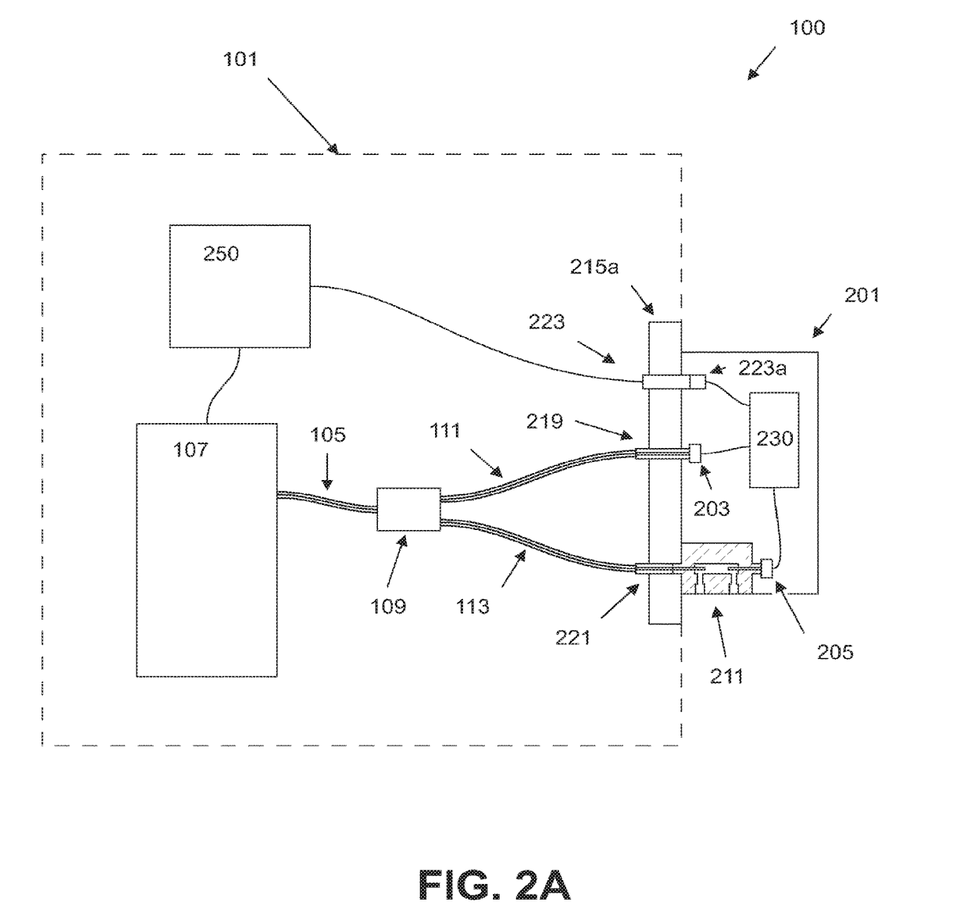
FIGS. 2A to 2D show a schematic flow cell optical detection system in accordance with an embodiment of the invention.

The detector interface 215a may be a section of a monitor housing 101 as is schematically indicated in FIG. 2A, but it may be arranged remote to the light source 107 etc. In the disclosed embodiment the detector interface 215a is optically connected to the source of light 107 by a sample illumination fiber 113 and a reference fiber 111, and the detector unit is arranged to detect the relative difference between the sample illumination light after the flow cell 211 and the reference by means of photo detectors 205 and 203, respectively. The photo detectors 203 and 205 may be of any suitable type capable of detecting light of the selected wavelength, such as photo diodes or the like. In one embodiment, the photo detectors are provided as a matched pair.

In one embodiment, the flow cell 211 is optically connected to the detector unit 201 by a fixed connector, and to the detector interface 215a by a self adjusting optical connector 221. In the disclosed embodiment, the detector interface is optically connected to the source of light by one or more optical fibers. But in alternative embodiments (not shown), the detector interface may be a section of a monitor housing (schematically indicated by ref 101) and the light from the light source 107 is output directly to the connector 221 and into the flow cell without passing an optic fiber.

Figure 2B:
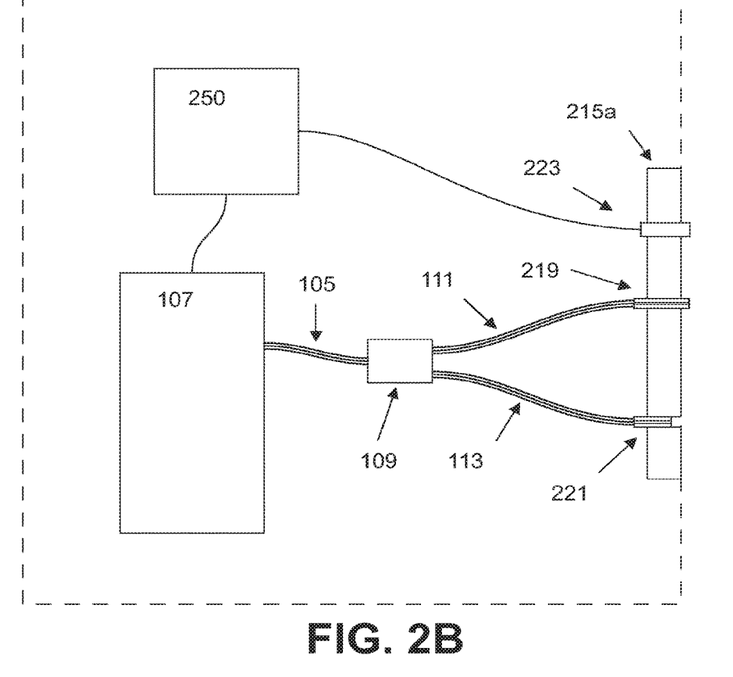
Figure 2C:
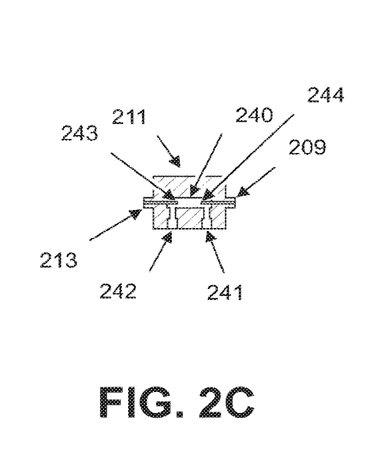
Figure 2D:
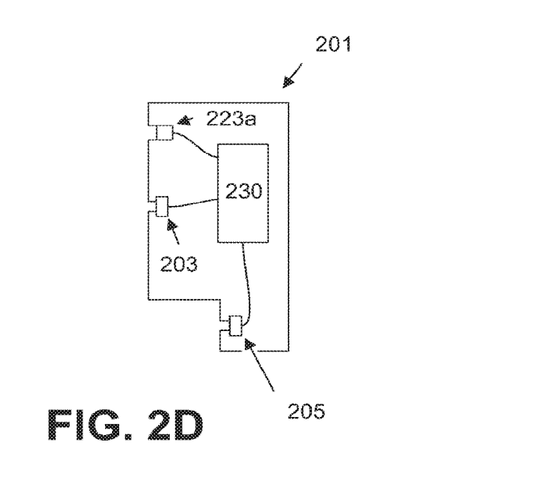

FIG. 2B shows the optical detection system 100 of FIG. 2A wherein the Detector unit 201 and the flow cell 211 are detached from the detector interface 215a. FIG. 2C shows a schematic cross section of a flow cell 211 in accordance with one embodiment of the present invention. The flow cell 211 comprises optical connectors 213 and 209 and a fluid inlet 242 and a fluid outlet 241 for connecting the flow cell 211 to a fluidic system for providing the sample fluid flow in a measurement cell 240. Light is supplied into the measurement cell 240 via light guide 243 and is collected by light guide 244 which in turn transmits the collected light to the sample photodiode 205.

Figure 3:
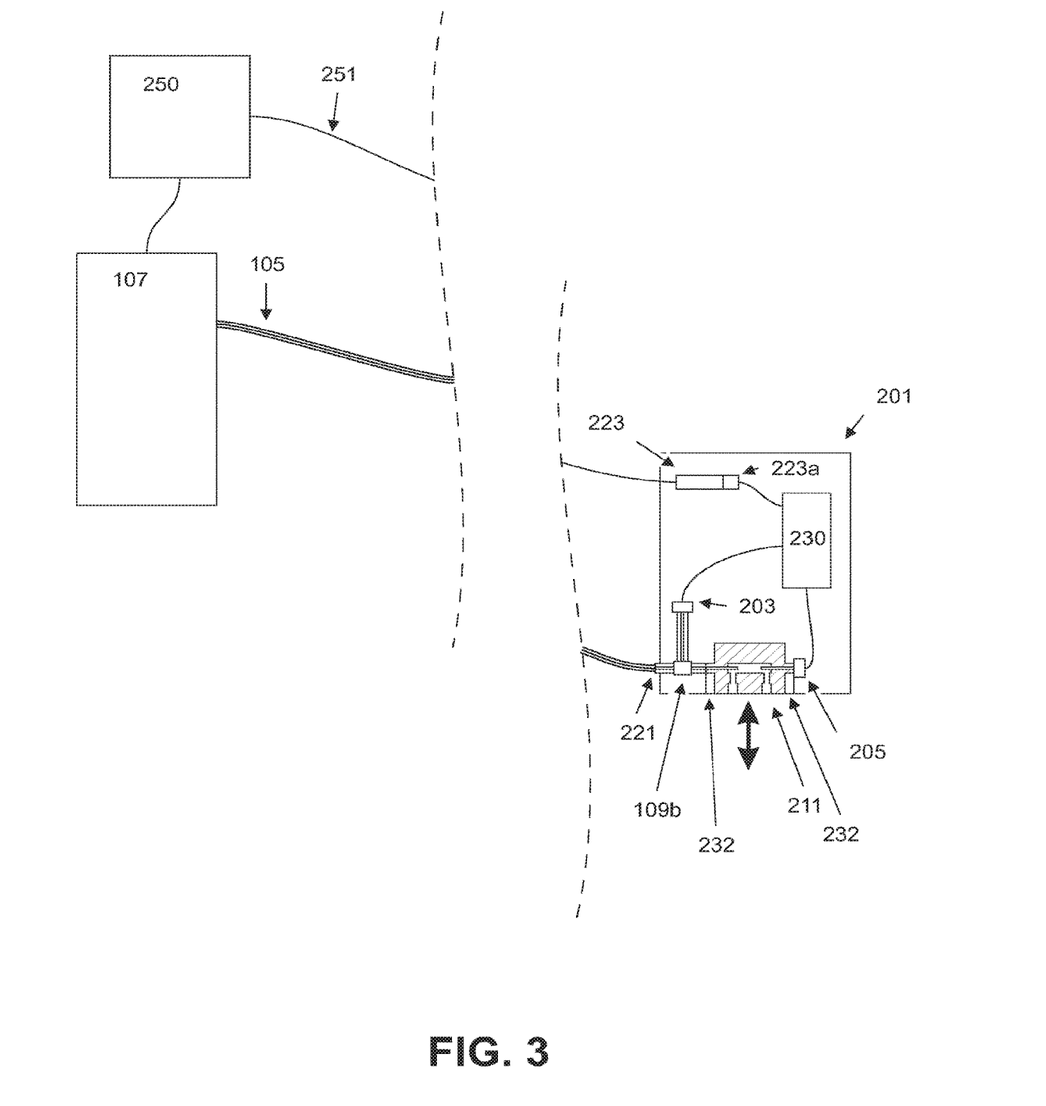
FIG. 3 shows a flow cell optical detection system in accordance with another embodiment of the invention.

FIG. 3 discloses an alternative embodiment of the optical detection system 100, wherein the detector unit 201 is integrated with the detector interface and comprises an optical splitter 109b unit for diverting reference light to the reference photo detector 203 from the light supplied by the light source via fiber 105. In this embodiment, the flow cell 211 is releasably attached to the detector unit by means of connector groves 232. Moreover, the detector unit is schematically disclosed as being arranged remotely to the light source etc, interconnected to the light source by the optic fiber 105 and in remote communication with a system controller 250 or the like by wire 251. According to one embodiment, the detector unit 201 may comprise one detector and a beam-chopper to alter which beam that illuminates the one detector.

The light source, such as a monochromator unit, is delicate and need to be placed in a stable and vibration free environment, whereas the detection unit may be a rigid solid state unit that is capable of being placed at more exposed positions, remote to the monochromator unit. This may be beneficial in situations where it is desired to perform measurements close to process equipment or the like.

According to other embodiments, the detector interface 215a may be arranged as a section of an external face of a monitor housing.

Figure 4:
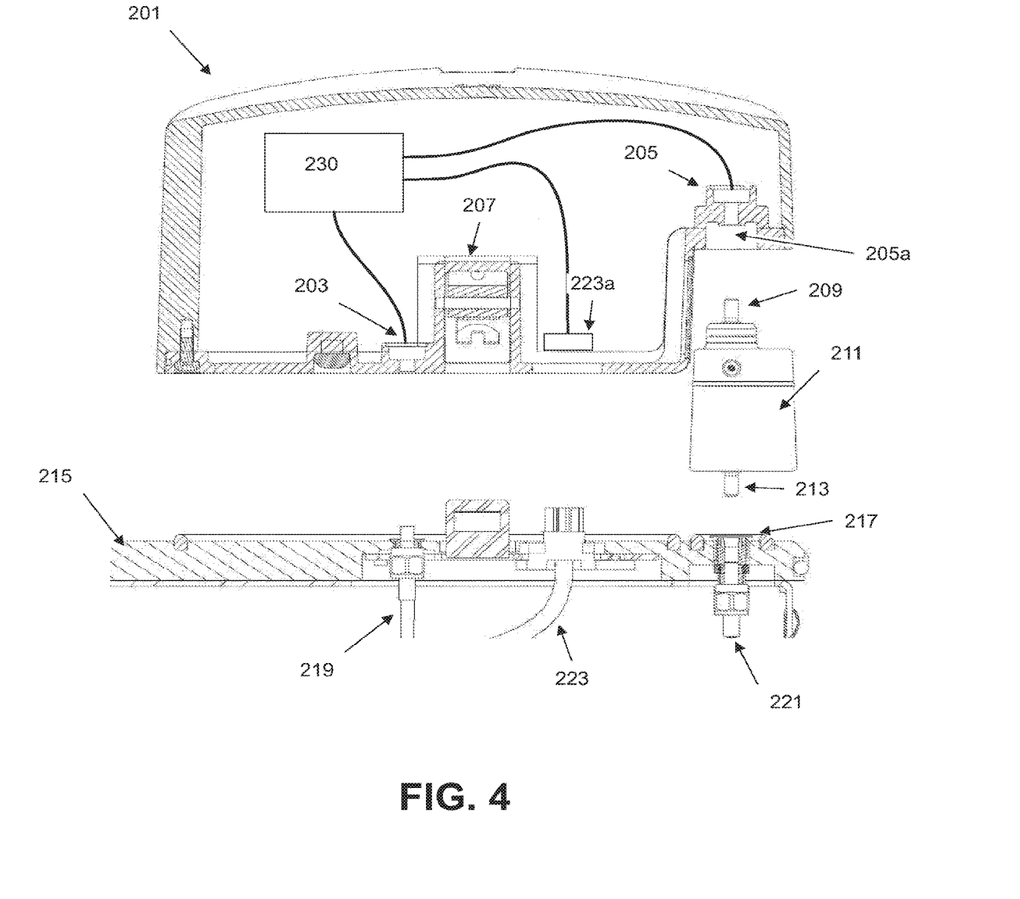
FIG. 4 shows a detector housing, a flow cell and a monochromator housing in accordance with an embodiment of the invention.

FIG. 4 shows an example of a new detector 201, a flow cell 211 and parts of a monitor or monochromator housing 215. The monitor housing 215 may be referred to as a second housing. The detector or detector housing 201 or a first housing includes: a reference photo diode 203, a sample photo diode 205 and a locking mechanism 207. Next to the detector housing 201 is an interchangeable flow cell 211; this flow cell 211 has an optical output end, herein referred to as the top portion, that includes a first fiber connector 209 and an optical input end, herein referred to as the bottom portion, of the interchangeable flow cell 211 that includes a second fiber connector 213. Fiber connector 213 may have any type of shape, such as a cylindrical or a conical shape. Adjacent to the interchangeable flow cell 211, there is the monitor housing 215 that includes the following components: a reference fiber 219, a sample fiber 221, an electrical cable connector 223 with a floating electrical connector and a floating connector 217. The floating connector 217 is a floating, spring loaded splicing adaptor. Reference fiber 219, and a sample fiber 221 are precisely aligned in their connectors of the housing 215. In another embodiment of the invention, the flow cell 211 may not be directly attached to the monochromator. The flow cell 211 only needs an optical fiber to guide light from the optical fiber connector 221.

In the disclosed embodiment the detector 201 comprises detector electronics 230 arranged to collect and optionally evaluate the output from the reference photodiode 203 and the sample photodiode 205. The detector electronics 230 are arranged to communicate with a main control system or other data collection system via the connector 223.

The top portion 209 of the interchangeable flow cell 211 engages a hole or a receptacle 205a of the sample photo diode 205 of the detector housing 201. The top portion 209 of the interchangeable flow cell 211 has a fixed position. Next, the bottom portion 213 of the interchangeable flow cell 211 is movably inserted into a receptacle 217a or a hole of the splicing connector 217 of the monitor housing 215. In order for the top portion 209 of the interchangeable flow cell to engage the sample photo diode 205, there is an alignment between the top portion 209 and the narrow bore receptacle 205a.

Figure 5:
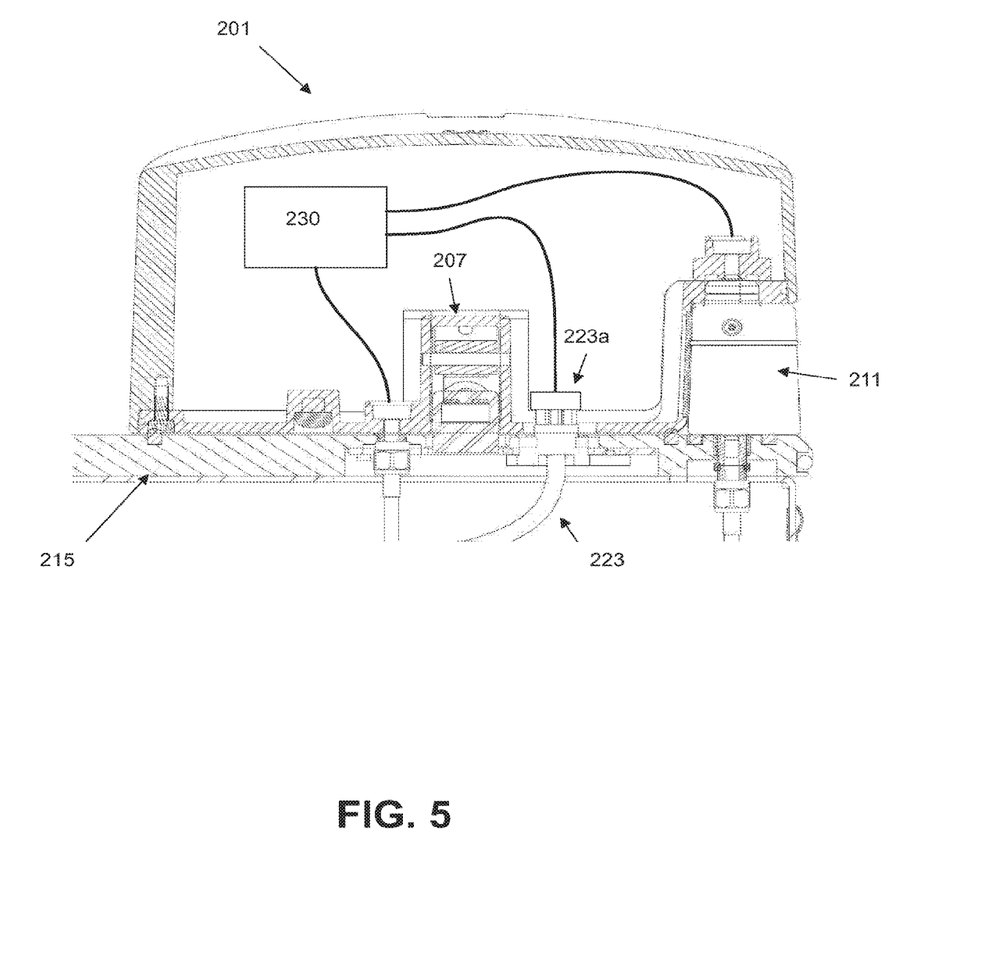
FIG. 5 shows a detector housing connected by the flow cell to a monochromator of FIG. 2 in accordance with an embodiment of the invention.

The bottom portion 213 of the interchangeable flow cell 211 is guided at first with a conical shaped entrance or receptacle 217a of a floating splice adaptor 217 of the monitor housing 215. The splicing connector 217 utilizes its spring-loaded mechanism to move itself in or out of position in order to receive the bottom portion 213 and also to meet the sample fiber 221. The sample fiber 221 may be referred to as optical fiber connector 221. Sample fiber 221 and its floating splicing adaptor also moves in an x, y, z direction and sample fiber 221 moves a certain angle in the range of 0 to 10 degrees. Also, the sample fiber 221 may be moved along a z direction, in the range 0 mm to 2 mm. The sample fiber 221 and its floating splicing adaptor 217 move in the x, y, and z directions and move a certain angle in order to meet the bottom portion 213 of the UV cell 211. The splice connector 217 moves in the left sideway, right sideway, up and down directions or at a tilted angle from 0 to 10 degrees. This left sideway or right sideway movement is +/−0.3 mm. For example, the splice connector 217 moves in a z direction by a spring at the splice connector 217 that brings the splice connector 217 forward towards the interchangeable flow cell 211. The movement in the z direction is to ensure that the distances between the fibers are correct in the splice connector 217 in spite of different lengths of the flow cell 211 with its connectors 213 and 209. After the bottom portion of the flow cell 211 is secured to the monitor housing 215, then the detector housing 201 is secured to the monitor housing 215 by the locking mechanism 207 as shown in FIG. 5.

Figure 6:
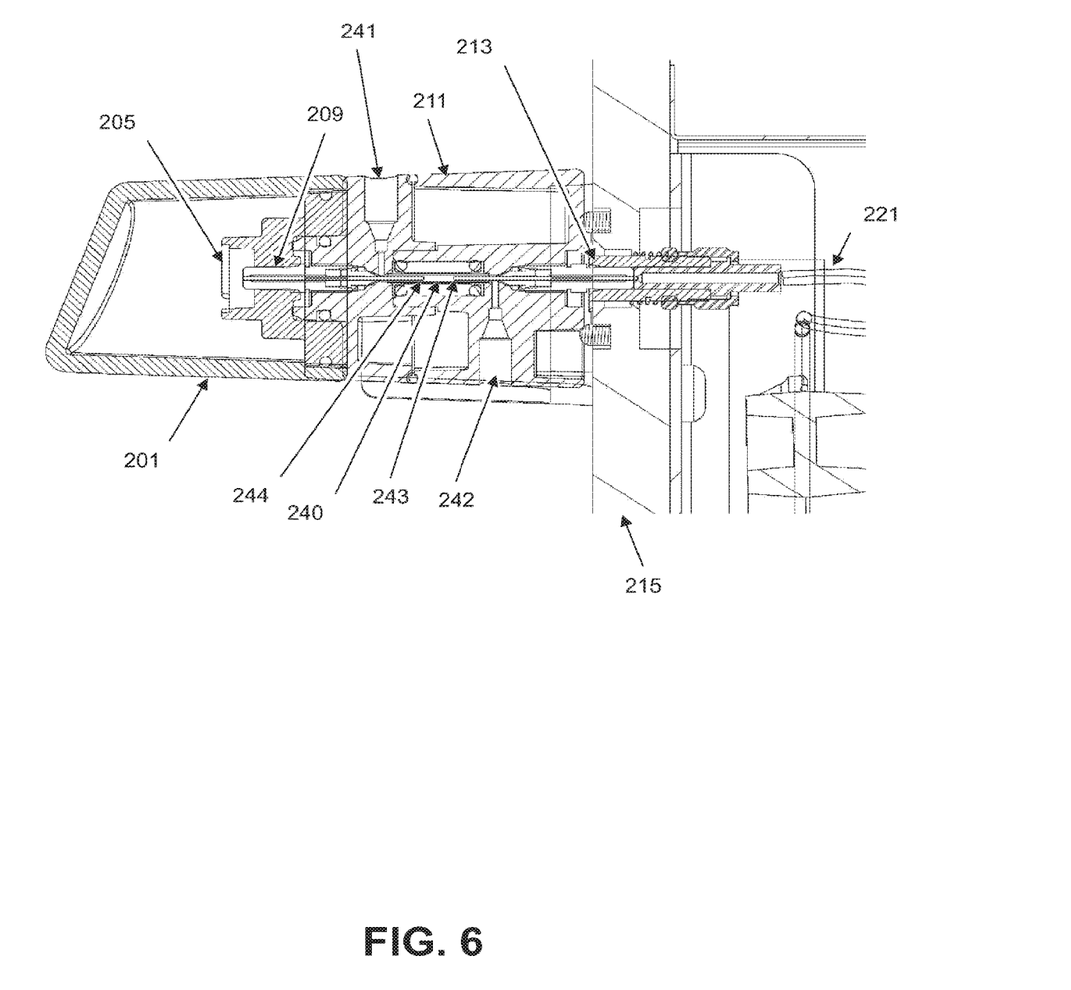
FIG. 6 shows a schematic of a section cut of the detector housing and the monochromator of FIG. 2 in accordance with an embodiment of the invention.

FIG. 6 shows a schematic section cut of the detector 201, the flow cell 211 and the monitor housing 215. At this view, the flow cell 211 is located in between the detector housing 201 and the monitor housing 215. Specifically, the top portion 209 of the flow cell 211 is in the detector housing 201 and the bottom portion 213 of the flow cell 211 is in the monitor housing 215. In the disclosed embodiment, the flow cell comprises a fluid inlet 242 and a fluid outlet 241 for connecting the flow cell 211 to a fluidic system for providing the sample fluid flow in a measurement cell 240. Light is supplied into the measurement cell 240 via light guide 243 and is collected by light guide 244 which in turn transmits the collected light to the sample photodiode 205.

Figure 7:
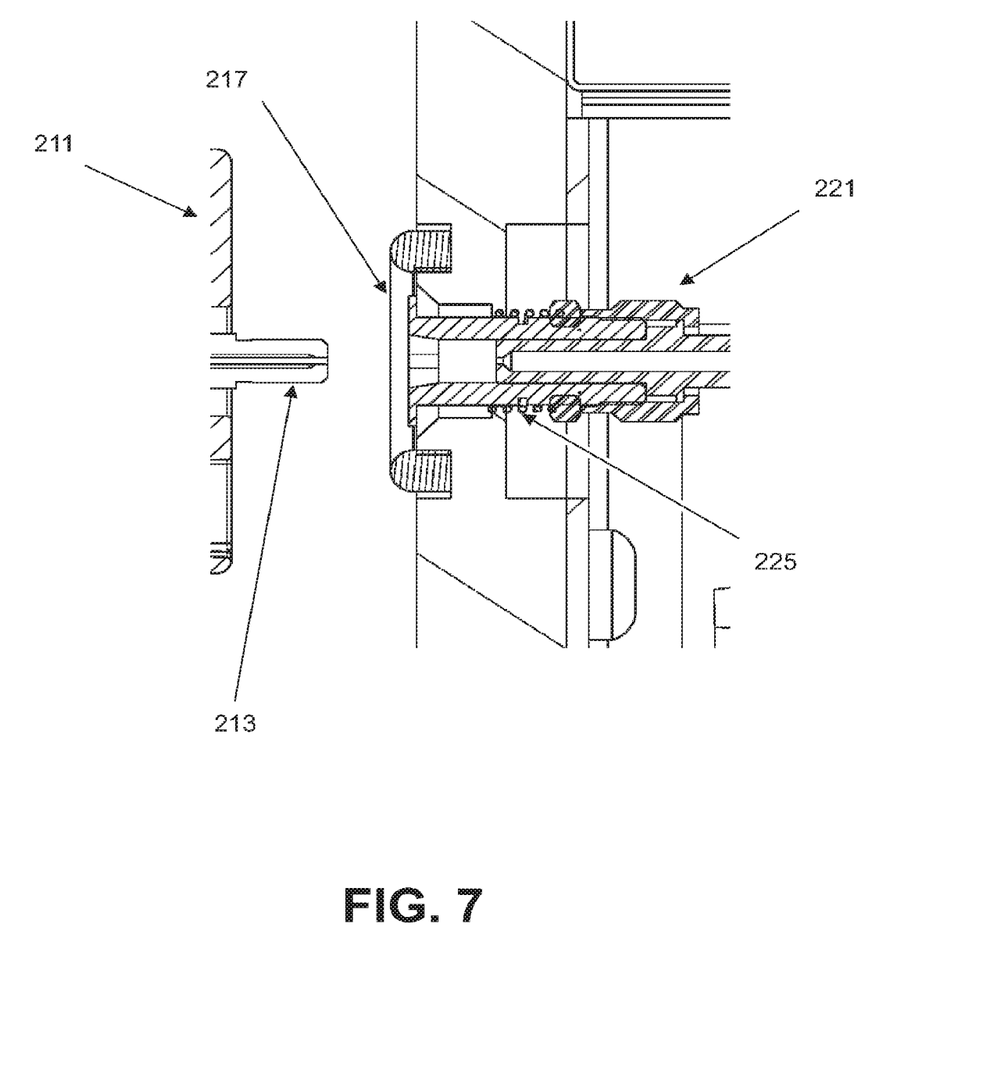
FIG. 7 is a schematic of connecting parts in a fiber system of the detector housing, UV Cell and the monochromator in accordance with an embodiment of the invention.
Figure 8A:
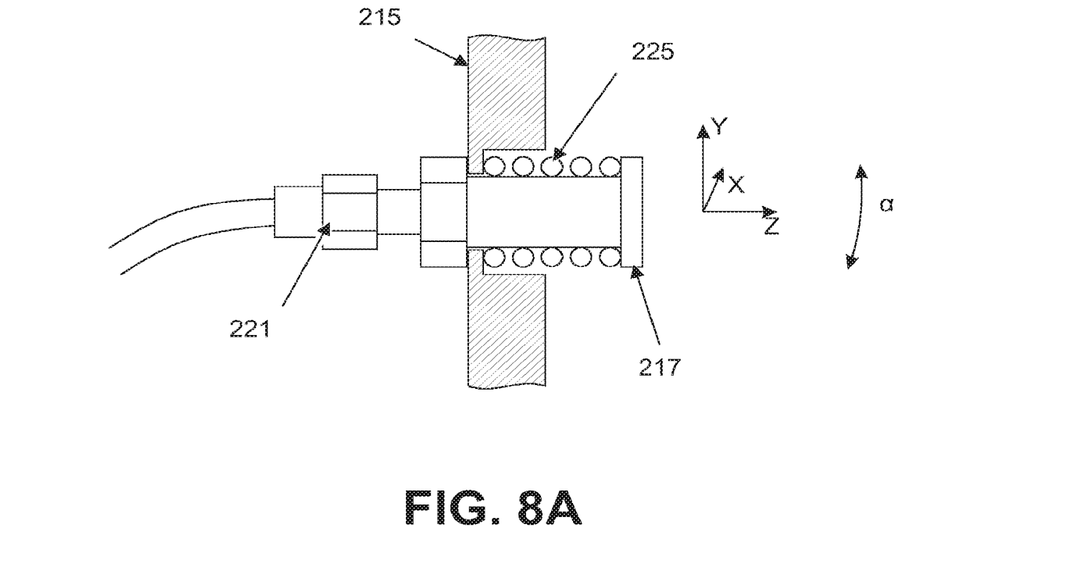
FIGS. 8A and 8B illustrate the movement of the optical fiber of FIG. 5 in accordance with an embodiment of the invention.
Figure 8B:
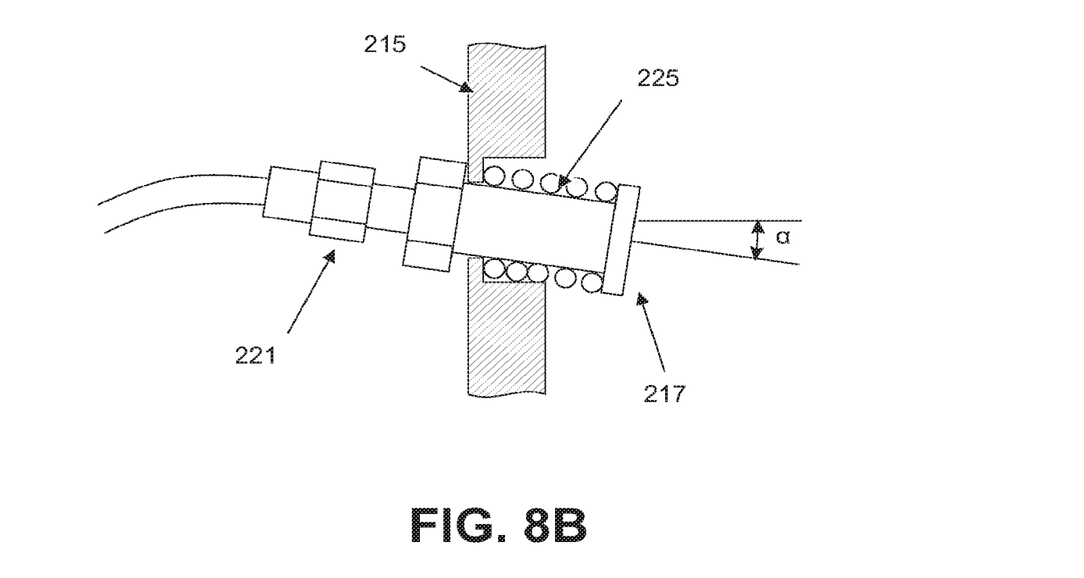

FIG. 7 is a schematic of connecting parts in the fiber system of the monitor housing and the UV cell of FIG. 4. The monitor housing 215 includes: a fiber connector 221, a floating splicing adaptor 217 and a spring 225 located outside of the floating splicing adaptor 217. The UV cell 211 or flow cell includes a fiber connector 213. As shown in FIG. 8A, fiber splicing adaptor 217 moves in an x, y, z direction and the fiber splicing adaptor 217 also moves a certain angle, α, in the range of 0 to 10 degrees (FIG. 8B). Also, the fiber splicing adaptor 217 may be moved along a z direction as in FIG. 8A. The fiber connector 213 moves splicing adaptor 217 in the x, y, and z directions and moves a certain angle in order to meet the fiber connector 213.

The connector 213 of the UV cell 211 is shaped or configured to fit into the floating splicing adaptor 217 and meet the fiber connector 221 at a distance of 0.01 mm to 0.1 mm. A movement of the UV cell and its connector 213 in the X, Y and Z directions and in a tilting motion of 0 to 10 degrees allows it still to fit into the floating splicing adaptor 217 of the monitor housing 215. The fiber splicing adaptor 217 has a floating part that is spring loaded to allow fiber connector 221 to move in several different directions, as discussed above, between the UV cell 211 and the monitor housing 215 to ensure that the fiber connectors 213 and 221 are at a correct distance. The floating splicing adaptor 217 enables the UV cell 211 to be easily inserted into the monitor housing 215.

Figure 9A:
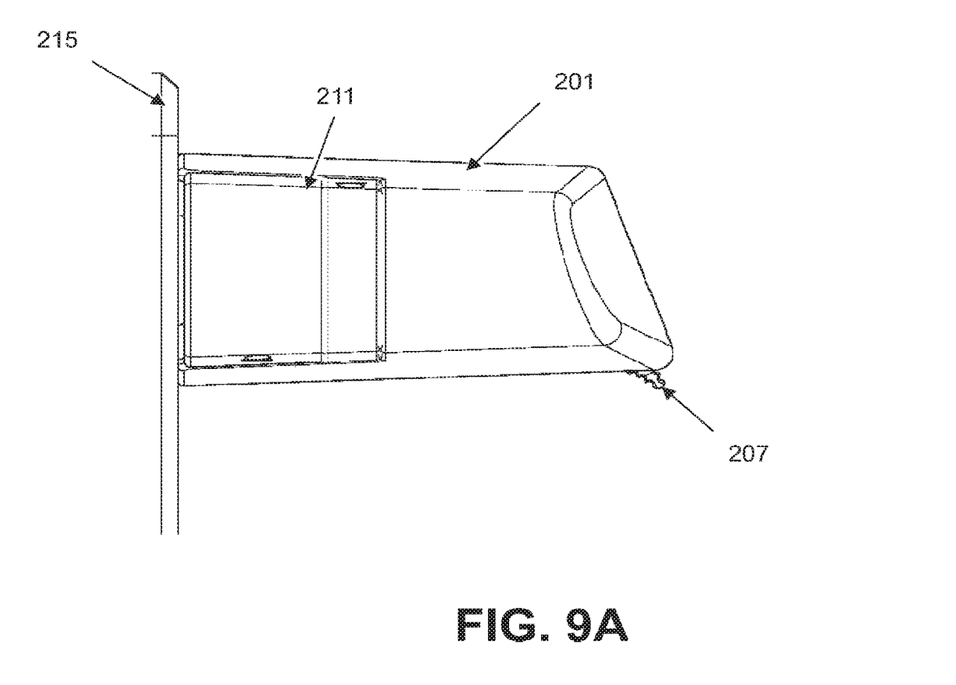
FIGS. 9A and 9B shows a schematic of the optical fiber system in an external view and internal view.
Figure 9B:
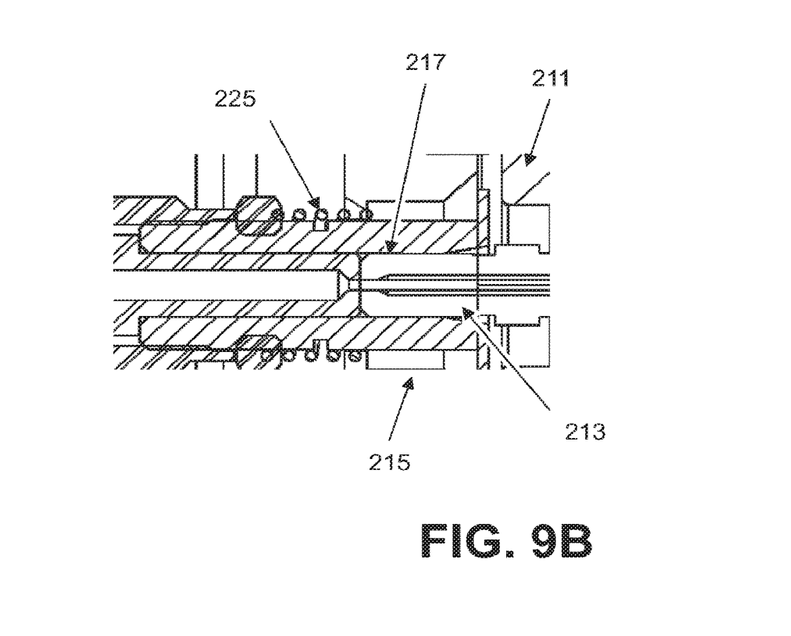

FIG. 9A shows a schematic of the detector housing and flow cell assembled to the monitor housing with no visible fibers. In this figure, the UV cell 211 is inserted in between the detector housing 201 and the monitor housing 215. In order to secure the fiber connector 213 in the floating splicing adaptor 217 the latch mechanism 207 is used as an external force. FIG. 9B shows the connector 213 inserted in the floating splicing adaptor. The floating splicing adaptor 217 and its spring 225 adjusts its position so the fiber connector 221 can receive the fiber connector 213 of the UV cell 211 at a correct position and distance.

This embodiment provides an apparatus that enables a user to easily remove and change a flow cell located there between monitor housing and detector housing. Also, this invention protects sensitive optical fiber and detector electronics, which minimizes disturbances to the optical fiber and detector electronics. Further, this embodiment provides the user with a solution that is a fast and easy to assemble or disassemble a UV cell from a monochromator and a detector housing without any tools.

Although the present invention has been described and illustrated in detail, it is to be clearly understood that this is done by way of illustration and example only and is not to be taken by way of limitation. The scope is to be limited only by the terms of the appended claims.

What is claimed is:

1. A method of using a flow cell optical detection system having a first detachable unit comprising a light source, a second detachable unit operably engageable to the first detachable unit comprising a first and a second detectors, and a detachable liquid flow cell operably engageable to the first and the second detachable units, the method comprising:
   releasably engaging the first detachable unit and the second detachable unit with each other to operably sandwich the flow cell between the first detachable unit and the second detachable unit forming a sample or second optical connection from the light source through the flow cell to the second detector following a second optical path while simultaneously forming a first optical connection between the light source and the first detector following a first optical path to form the flow cell optical detection system, and,
   detecting a sample signal with the optical detection system.

2. The method of claim 1, wherein the first detachable unit comprises a housing, an interface mounted thereon, an optical path connector of the first unit on the interface, a flow cell connector on the interface, and the light source where a light beam from the light source is split into a first light beam and a second light beam by an optical splitter to go through the first optical path in the system and the second optical path in the system respectively;
   wherein the second detachable unit comprises the first detector on the first optical path, the second detector on the second optical path, an optical path connector of the second unit, and a flow cell connector of the second unit;
   wherein the detachable liquid flow cell comprises a first unit connector and a second unit connector,
   wherein the first optical connection is provided through the engagement of the optical path connector of the first unit on the interface with the optical path connector of the second unit,
   wherein the second or sample optical connection is provided by the engagement of the first unit connector of the flow cell and the flow cell connector of the first unit and the second unit connector of the flow cell with the flow cell connector of the second unit such that the flow cell is sandwiched between the units when the first unit is releasably attached to the second unit and the flow cell is optically connected to the second detector along the second optical path.

3. The method of claim 1, wherein the second unit includes electronics configured to process signals from the first and second detectors to compute a difference between signals from the first and second detectors.

4. The method of claim 2, wherein the first light beam is a reference light beam and the first detector is associated with the reference light beam from the light source through the first optical path and the second light beam is a sample light beam and the second detector is associated with the flow cell and the sample light beam from the light source through the second optical path.

5. The method of claim 1, further comprising detaching the first and second detachable units from the flow cell to release the flow cell and releasably engaging a new flow cell with the first and the second detachable units to form a new operable flow cell optical detection system.

6. The method of claim 1, wherein the first unit connector is spring-loaded splicing adaptor.

7. The method of claim 1, wherein the light source is configured to output one of ultraviolet light and visible light.

8. The method of claim 1, further comprising detaching the first detachable unit and replace it with a new detachable unit.

9. The method of claim 1, further comprising detaching the second detachable unit and replace it with a new second detachable unit.

10. The method of claim 1, wherein the detectors are located at a remote location with respect to the light source.

11. A method of using a flow cell optical detection system having a first detachable unit comprising a light source, a second detachable unit operably engageable to the first detachable unit comprising at least a sample detector, a reference detector and a detachable flow cell operably engageable to the first and the second detachable units, the method comprising:

releasably engaging the first detachable unit and the second detachable unit with each other to operably sandwich the flow cell between the first detachable unit and the second detachable unit forming a sample optical connection from the light source, through the flow cell to the sample detector following a sample optical path while simultaneously forming a reference optical connection between the light source and the reference detector following a reference optical path to form the flow cell optical detection system, and detecting a sample signal with the optical detection system.

12. The method of claim 11, wherein the light source is configured to output one of ultraviolet light and visible light.

13. The method of claim 11, wherein the second unit includes electronics configured to process signals from the reference and sample detectors to compute a difference between signals from the reference and sample detectors.

14. The method of claim 11, further comprising detaching the flow cell to replace it with a new flow cell.

15. The method of claim 11, further comprising detaching the first detachable unit and replace it with a new detachable unit.

16. The method of claim 11, further comprising detaching the second detachable unit and replace it with a new second detachable unit.

17. The method of claim 11, wherein the detector is located at a remote location with respect to the light source.

18. The method of claim 11, wherein the first detachable unit comprises a housing, an interface mounted thereon, an optical path connector of the first unit on the interface, a flow cell connector on the interface, and the light source, wherein the light beam from the light source are split into a reference light beam and a sample light beam by an optical splitter to go through the reference optical path in the system and the sample optical path in the system respectively;

wherein the second detachable unit comprises the reference detector on the reference optical path, the sample detector on the sample optical path, an optical path connector of the second unit, and a flow cell connector of the second unit;

wherein the detachable liquid flow cell including a first unit connector and a second unit connector, wherein the flow cell is detachable from the first and the second units;

wherein the reference optical connection is provided through the engagement of the optical path connector of the first unit on the interface with the optical path connector of the second unit, wherein the sample optical connection is provided by the engagement of the first unit connector of the flow cell and the flow cell connector of the first unit and the second unit connector of the flow cell with the flow cell connector of the second unit such that the flow cell is sandwiched between the units when the first unit is releasably attached to the second unit and the flow cell is optically connected to the second detector along the sample optical path, and wherein the second unit connector is an optical fiber connector and the first unit connector is a self-adjusting optical connector.

19. The method of claim 18, wherein the reference detector is associated with the reference light beam from the light source through the reference optical path and the sample detector is associated with the flow cell and the sample light beam from the light source through the sample optical path.

20. The method of claim 18, wherein the self-adjusting optical connector is a spring-loaded splicing adaptor.

* * * * *